US006821646B2

(12) United States Patent
Tsuboyama et al.

(10) Patent No.: US 6,821,646 B2
(45) Date of Patent: Nov. 23, 2004

(54) LUMINESCENCE DEVICE, DISPLAY APPARATUS AND METAL COORDINATION COMPOUND

(75) Inventors: Akira Tsuboyama, Sagamihara (JP); Hidemasa Mizutani, Sagamihara (JP); Shinjiro Okada, Isehara (JP); Takao Takiguchi, Tokyo (JP); Seishi Miura, Sagamihara (JP); Takashi Moriyama, Kawasaki (JP); Satoshi Igawa, Fujisawa (JP); Jun Kamatani, Kawasaki (JP); Manabu Furugori, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/960,285

(22) Filed: Sep. 24, 2001

(65) Prior Publication Data

US 2002/0063516 A1 May 30, 2002

(30) Foreign Application Priority Data

Sep. 26, 2000 (JP) ........................................ 2000/292490
Nov. 28, 2000 (JP) ........................................ 2000/360569
Jun. 25, 2001 (JP) ........................................ 2001/190866
Sep. 19, 2001 (JP) ........................................ 2001/284600

(51) Int. Cl.$^7$ .......................... H05B 33/14; C09K 11/06
(52) U.S. Cl. ........................ 428/690; 428/917; 313/504; 544/225; 546/4; 549/3
(58) Field of Search .............................. 428/690, 917; 313/504; 252/301.16; 544/225, 235, 238, 253; 546/2, 4, 10; 548/101, 364.1, 364.4, 364.7; 549/3, 29, 49, 59

(56) References Cited

U.S. PATENT DOCUMENTS

| 5,698,858 | A | 12/1997 | Börner ..................... 250/484.2 |
| 2001/0019782 | A1 * | 9/2001 | Igarashi et al. ............. 428/690 |
| 2002/0034656 | A1 * | 3/2002 | Thompson et al. ......... 428/690 |
| 2002/0121638 | A1 * | 9/2002 | Grushin et al. ............... 257/40 |

FOREIGN PATENT DOCUMENTS

| JP | 8-319482 | 12/1996 |
| JP | 11-256148 | 9/1999 |
| JP | 11-329739 | 11/1999 |
| JP | 20001-181616 | 7/2001 |

OTHER PUBLICATIONS

Maestri et al., "Photochemistry and Luminescence of Cyclometallated Complexes", Advances in Photochemistry, vol. 17, pp. 1–68, 1992.*
C.H. Chen et al., "Recent Developments in Molecular Organic Electroluminescent Materials," 125 *Macromol. Symp.* 1–48 (19970.
D.F. O'Brien et al., "Improved Energy Transfer in Electrophosphorescent Devices," 74(3) *Appl. Phys. Lett.* 442–444 (Jan. 18, 1999).
M.A. Baldo et al., "Very High–Efficiency Green Organic Light–Emitting Devices Based on Electrophosphorescence," 75(1) *Appl. Phys. Lett.* 4–6 (Jul. 5, 1999).
Chihaya Adachi et al., "High–Efficiency Organic Electrophosphorescent Devices with Tris(2–phenylpyridine)iridium Doped into Electron–Transporting Materials," 77(6) *Appl. Phys. Lett.* 904–906 (Aug. 7, 2000).
Vladimir V. Grushin et al., "New, Efficient Electroluminescent Materials Based on Organometallic Ir Complexes," *Chem. Commun.* 1494–1495 (Jul. 23, 2001).
European Search Report in Application No. 01122937.4 (Apr. 17, 2003).

* cited by examiner

*Primary Examiner*—Marie Yamnitzky
(74) *Attorney, Agent, or Firm*—Fitzpatrick, Cella, Harper & Scinto

(57) ABSTRACT

A luminescence device that has an organic compound layer disposed between a pair of electrodes. This organic compound layer contains a metal coordination compound represented by the following formula (1)

$$M \left[ \begin{array}{c} CyN \\ | \\ CyC \end{array} \right]_n \quad (1)$$

wherein M is Ir, Rh or Pd; n is 2 or 3; CyN is a substituted or unsubstituted cyclic group containing a nitrogen atom connected to M and capable of containing another nitrogen atom and/or sulfur atom; and CyC is a substituted or unsubstituted cyclic group containing a carbon atom connected to M and capable of containing a nitrogen atom and/or a sulfur atom.

6 Claims, 1 Drawing Sheet

LUMINESCENCE DEVICE, DISPLAY APPARATUS AND METAL COORDINATION COMPOUND

FIELD OF THE INVENTION AND RELATED ART

The present invention relates to a luminescence device, a display apparatus and a metal coordination compound therefor. More specifically, the present invention relates to a luminescence device employing an organic metal coordination compound having a formula (1) appearing hereinafter as a luminescence material so as to allow stable luminescence efficiency, a display apparatus including the luminescence device and the metal coordination compound adapted for use in the luminescence device.

An organic electroluminescence (EL) device has been extensively studied as a luminescence device with a high responsiveness and high efficiency.

The organic EL device generally has a sectional structure as shown in FIG. 1A or 1B (e.g., as described in "Macromol. Symp.", 125, pp. 1–48 (1997)).

Referring to the figures, the EL device generally has a structure including a transparent substrate 15, a transparent electrode 14 disposed on the transparent substrate 15, a metal electrode 11 disposed opposite to the transparent electrode 14, and a plurality of organic (compound) layers disposed between the transparent electrode 14 and the metal electrode 11.

Referring to FIG. 1, the EL device in this embodiment has two organic layers including a luminescence layer 12 and a hole transport layer 13.

The transparent electrode 14 may be formed of a film of ITO (indium tin oxide) having a larger work function to ensure a good hole injection performance into the hole transport layer. On the other hand, the metal electrode 11 may be formed of a layer of aluminum, magnesium, alloys thereof, etc., having a smaller work function to ensure a good electron injection performance into the organic layer (s).

These (transparent and metal) electrodes 14 and 11 may be formed in a thickness of 50–200 nm.

The luminescence layer 12 may be formed of, e.g., aluminum quinolinol complex (representative example thereof may include Alq3 described hereinafter) having an electron transporting characteristic and a luminescent characteristic. The hole transport layer 13 may be formed of, e.g., triphenyldiamine derivative (representative example thereof may include α-NPD described hereinafter) having an electron donating characteristic.

The above-described EL device exhibits a rectification characteristic, so that when an electric field is applied between the metal electrode 11 as a cathode and the transparent electrode 14 as an anode, electrons are injected from the metal electrode 11 into the luminescence layer 12 and holes are injected from the transparent electrodes 14.

The thus-injected holes and electrons are recombined within the luminescence layer 12 to produce excitons, thus causing luminescence. At that time, the hole transport layer 13 functions as an electron-blocking layer to increase a recombination efficiency at the boundary between the luminescence layer 12 and the hole transport layer 13, thus enhancing a luminescence efficiency.

Referring to FIG. 1B, in addition to the layers shown in FIG. 1A, an electron transport layer 16 is disposed between the metal electrode 11 and the luminescence layer 12, whereby an effective carrier blocking performance can be ensured by separating functions of luminescence, electron transport and hole transport, thus allowing effective luminescence.

The electron transport layer 16 may be formed of, e.g., oxadiazole derivatives.

In ordinary organic EL devices, fluorescence caused during a transition of luminescent center molecule from a singlet excited state to a ground state is used as luminescence.

On the other hand, not the above fluorescence (luminescence) via singlet exciton, phosphorescence (luminescence) via triplet exciton has been studied for use in organic EL device as described in, e.g., "Improved energy transfer in electrophosphorescent device" (D. F. O'Brien et al., Applied Physics Letters, Vol. 74, No. 3, pp. 442–444 (1999)) and "Very high-efficiency green organic light-emitting devices based on electrophosphorescence" (M. A. Baldo et al., Applied Physics Letters, Vol. 75, No. 1, pp. 4–6 (1999)).

The EL devices shown in these documents may generally have a sectional structure shown in FIG. 1C.

Referring to FIG. 1C, four organic layers including a hole transfer layer 13, a luminescence layer 12, an exciton diffusion-prevention layer 17, and an electron transport layer 16 are successively formed in this order on the transparent electrode (anode) 14.

In the above documents, higher efficiencies have been achieved by using four organic layers including a hole transport layer 13 of α-NPD (shown below), an electron transport layer 16 of Alq3 (shown below), an exciton diffusion-prevention layer 17 of BPC (shown below), and a luminescence layer 12 of a mixture of CPB (shown below) as a host material with Ir(ppy)$_3$ (shown below) or PtOEP (shown below) as a guest phosphorescence material doped into CBP at a concentration of ca. 6 wt. %.

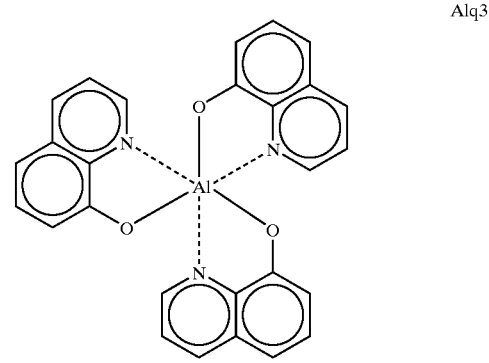

Alq3

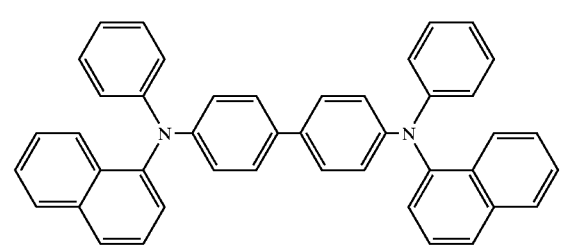

α-NPD

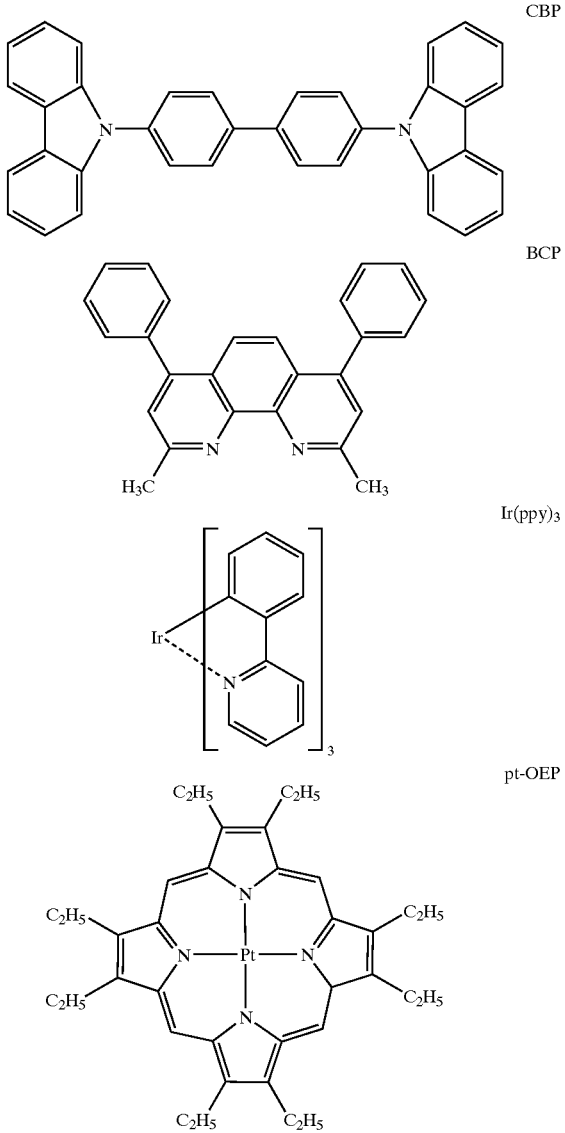

Alq3: tris(8-hydroxyquinoline) aluminum (aluminum-quinolinol complex),

α-NPD: N4,N4'-di-naphthalene-1-yl-N4,N4'-diphenyl-biphenyl-4,4'-diamine (4,4'-bis[N-(1-naphthyl)-N-phenyl-amino]biphenyl), CBP: 4,4'-N,N'-dicarbazole-biphenyl, BCP: 2,9-dimethyl-4,7-diphenyl-1,10-phenan-throline, Ir(ppy)₃: fac tris(2-phenylpyridine)iridium (iridium-phenylpyridine complex), and PtEOP: 2,3,7,8,12,13,17,18-octaethyl-21H,23H-porphine platinum (platinum-octaethyl porphine complex).

The phosphorescence (luminescence) material used in the luminescence layer 12 has attracted notice. This is because the phosphorescence material is expected to provide a higher luminescence efficiency in principle.

More specifically, in the case of the phosphorescence material, excitons produced by recombination of carriers comprise singlet excitons and triplet excitons presented in a ratio of 1:3. For this reason, when fluorescence caused during the transition from the singlet excited state to the ground state is utilized, a resultant luminescence efficiency is 25% (as upper limit) based on all the produced excitons in principle.

On the other hand, in the case of utilizing phosphorescence caused during transition from the triplet excited state, a resultant luminescence efficiency is expected to be at least three times that of the case of fluorescence in principle. In addition thereto, if intersystem crossing from the singlet excited state (higher energy level) to the triplet excited state is taken into consideration, the luminescence efficiency of phosphorescence can be expected to be 100% (four times that of fluorescence) in principle.

The use of phosphorescence based on transition from the triplet excited state has also been proposed in, e.g., Japanese Laid-Open Patent Application (JP-A) 11-329739, JP-A 11-256148 and JP-A 8-319482.

However, the above-mentioned organic EL devices utilizing phosphorescence have accompanied with a problem of luminescent deterioration particularly in an energized state.

The reason for luminescent deterioration has not been clarified as yet but may be attributable to such a phenomenon that the life of triplet exciton is generally longer than that of singlet exciton by at least three digits, so that molecule is placed in a higher-energy state for a long period to cause reaction with ambient substance, formation of exciplex or excimer, change in minute molecular structure, structural change of ambient substance, etc.

Accordingly, the (electro)phosphorescence EL device is expected to provide a higher luminescence efficiency as described above, while the EL device is required to suppress or minimize the luminescent deterioration in energized state.

SUMMARY OF THE INVENTION

An object of the present invention is to provide a luminescence device capable of providing a high-efficiency luminescent state at a high brightness (or luminance) for a long period while minimizing the deterioration in luminescence in energized state.

Another object of the present invention is to provide a display apparatus including the luminescence device.

A further object of the present invention is to provide a metal coordination compound as a material suitable for an organic layer for the luminescence device.

According to the present invention, there is provided a luminescence device, comprising: an organic compound layer comprising a metal coordination compound represented by the following formula (1):

wherein M denotes Ir, Rh or Pd; n is 2 or 3; CyN denotes a substituted or unsubstituted cyclic group containing a nitrogen atom connected to M and capable of containing another nitrogen atom and/or a sulfur atom; and CyC denotes a substituted or unsubstituted cyclic group containing a carbon atom connected to M and capable of containing a nitrogen atom and/or a sulfur atom, CyN and CyC being connected to each other via a covalent bond, and each of substituents for CyN and CyC being selected from the group consisting of a halogen atom; nitro group; a trialkylsilyl group containing three linear or branched alkyl groups each independently having 1–8 carbon atoms; and a linear or branched alkyl group having 1–20 carbon atoms capable of including one or at least two non-neighboring methylene groups which can be replaced with —O—, —S—, —CO—, —CO—O—, —O—CO—, —CH=CH— or —C≡C— and capable of including a hydrogen atom which can be replaced with a fluorine atom; with the proviso that a sum of nitrogen atom and sulfur atom present in ring structures of CyN and CyC is at least 2.

According to the present invention, there is also provided a metal coordination compound, adapted for use in a luminescence device, represented by the following formula (1):

(1)

wherein M denotes Ir, Rh or Pd; n is 2 or 3; CyN denotes a substituted or unsubstituted cyclic group containing a nitrogen atom connected to M and capable of containing another nitrogen atom and/or a sulfur atom; and CyC denotes a substituted or unsubstituted cyclic group containing a carbon atom connected to M and capable of containing a nitrogen atom and/or a sulfur atom, CyN and CyC being connected to each other via a covalent bond, and each of substituents for CyN and CyC being selected from the group consisting of a halogen atom; nitro group; a trialkylsilyl group containing three linear or branched alkyl groups each independently having 1–8 carbon atoms; and a linear or branched alkyl group having 1–20 carbon atoms capable of including one or at least two non-neighboring methylene groups which can be replaced with —O—, —S—, —CO—, —CO—O—, —O—CO—, —CH=CH— or —C≡C— and capable of including a hydrogen atom which can be replaced with a fluorine atom; with the proviso that a sum of nitrogen atom and sulfur atom present in ring structures of CyN and CyC is at least 2.

The present invention provides a display apparatus including the above-mentioned luminescence device and drive means for driving the luminescence device.

These and other objects, features and advantages of the present invention will become more apparent upon a consideration of the following description of the preferred embodiments of the present invention taken in conjunction with the accompanying drawing.

DESCRIPTION OF THE PREFERRED EMBODIMENTS

Figure 1A:
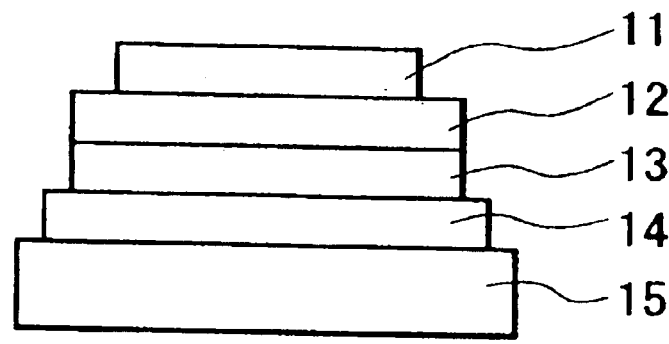
FIGS. 1A, 1B and 1C are respectively a schematic sectional view of a layer structure of a luminescence device.

In the case where a luminescence layer for an organic EL device is formed of a carrier transporting host material and a phosphorescent guest material, a process of emission of light (phosphorescence) may generally involve the following steps:

(1) transport of electron and hole within a luminescence layer,
(2) formation of exciton of the host material,
(3) transmission of excited energy between host material molecules,
(4) transmission of excited energy from the host material molecule to the guest material molecule,
(5) formation of triplet exciton of the guest material, and
(6) emission of light (phosphorescence) caused during transition from the triplet excited state to the ground state of the guest material.

In the above steps, desired energy transmission and luminescence may generally be caused based on various quenching and competition.

In order to improve a luminescence efficiency of the EL device, a luminescence center material per se is required to provide a higher yield of luminescence quantum. In addition thereto, an efficient energy transfer between host material molecules and/or between host material molecule and guest material molecule is also an important factor.

Further, the above-described luminescent deterioration in energized state may presumably relate to the luminescent center material per se or an environmental change thereof by its ambient molecular structure.

For this reason, our research group has extensively investigated an effect of use of the metal coordination compound of formula (1) as the luminescent center material and as a result, has found that the metal coordination compound of formula (1) allows a high-efficiency luminescence (e.g., luminescence efficiency of at least 1 cd/W) with a high brightness (luminance) for a long period (e.g., a luminance half-life of at least 500 hours at an initial luminance of 100 cd/m$^2$) (i.e., a decreased luminescent deterioration in energized state).

The metal coordination compound represented by the above formula (1) according to the present invention causes phosphorescence (luminescence) and is assumed to have a lowest excited state comprising a triplet excited state liable to cause metal-to-ligand charge transfer (MLCT* state). The phosphorescent emission of light (phosphorescence) is produced during the transition from the MLCT* state to the ground state.

The metal coordination compound of formula (1) according to the present invention has been found to provide a higher phosphorescence yield of 0.15–0.9 and a shorter phosphorescence life of 1–30 μsec.

A phosphorescence yield (P(m)) is obtained based on the following equation:

$$P(m)/P(s)=(S(m)/S(s))\times(A(s)/A(m)), \text{ wherein}$$

P(m) represents a phosphorescence yield of an (unknown) objective luminescent material, P(s) represents a known (standard) phosphorescence yield of standard luminescent material (Ir(ppy)$_3$), S(m) represents an integrated intensity of (photo-)excited emission spectrum of the objective material, S(s) represents a known integrated intensity of the standard material, A(m) represents an absorption spectrum of an excited light wavelength of the objective material, and A(s) represents a known absorption spectrum of the standard material.

The shorter phosphorescence life is necessary to provide a resultant EL device with a higher luminescence efficiency. This is because the longer phosphorescence life increases molecules placed in their triplet excited state which is a waiting state for phosphorescence, thus lowering the resultant luminescence efficiency particularly at a higher current density.

Accordingly, the metal coordination compound of formula (1) according to the present invention is a suitable luminescent material for an EL device with a higher phosphorescence yield and a shorter phosphorescence life.

Further, due to the shorter phosphorescence life, molecules of the metal coordination compound of formula (1) have a shorter time period wherein they stay in the triplet excited state, i.e. a higher energy state, thus providing the resultant EL device with improved durability and less deterioration in device characteristic. In this regard, the metal coordination compound according to the present invention has been substantiated to exhibit excellent stability of luminance as shown in Examples described hereinafter.

The metal coordination compound of formula (1) according to the present invention has a molecular structure wherein two or more nitrogen atom(s) and/or sulfur atom(s) in total in two ring structures constituting CyN and CyC, so that it becomes possible to decrease an energy gap, thus allowing a long-(emission) wavelength luminescence. This may be attributable to the following mechanism.

In the case where HOMO (highest occupied molecular orbital) and LUMO (lowest unoccupied molecular orbital) of molecular orbital for the centermetal M (in the formula (1)) and those (HOMO and LUMO) of molecular orbital for the ligands (in the formula (1)) are separately considered for convenience, energies of HOMO and LUMO for the ligands are lowered by the presence of nitrogen atom(s) and/or sulfu atom(s) to decrease an energy gap between HOMO for the center metal M and LUMO for the ligands, thus allowing luminescence from the MLCT* state (the lowest excited state) at a longer (emission) wavelength. Accordingly, the metal coordination compound of formula (1) according to the present invention is suitable luminescent material for luminescence at longer wavelength (orange to red).

Further, when an appropriate substituent is introduced into the ligand(s), an intermolecular interaction an occurrence of thermal quenching of excited molecules and improving device characteristics, such as film uniformity, electrical properties and device stability.

The luminescent material (metal coordination compound of formula (1)) of the present invention containing a plurality of nitrogen atom(s) and/or sulfur atom(s) in the ligands (ring structures), so that electron clouds may presumably considerably protruded from the ligands to promote interaction with other molecules via the nitrogen and/or sulfur atoms, thus improving energy transfer efficiency. As a result, it becomes possible to realize a luminescent material for longer wavelength (orange to red) with high efficiency and stability.

Further, the metal coordination compound of formula (1) according to the present invention has a molecular structure such that a plurality of identical ligands is bonded to the center metal M.

On the other hand, for example, yet-unreacted acetylacetonate ligand of iridium (III) acetylacetonate as used in Example 17 appearing hereinafter remains in the resultant metal coordination compound to provide a reaction product having a molecular structure wherein different ligands are bonded to a center metal in some cases. This metal coordination compound has a poor thermal stability and can cause thermal decomposition where an EL device is prepared through vacuum (vapor) deposition wherein the metal coordination compound is sublimated by resistance heating. Indeed the metal coordination compound containing acetylacetonate ligand has a lower initiation temperature for thermal decomposition, in addition to the poor thermal stability. As a result, the life of the resultant luminescence device using such a compound becomes shorter. Further, different ligands are present in the molecular structure of the metal coordination compound used in the luminescence device, so that electron levels for the different ligands are different from each other, thus adversely affecting electron transport performance.

In the case of phosphorescent (luminescent) material, luminescent characteristics are largely affected by its molecular environment. On the other hand, principal characteristics of the fluorescent material are studied based on photoluminescence.

For this reason, results of photoluminescence of the phosphorescent material do not reflect luminescent characteristics of the resultant EL device in many cases since the luminescent characteristics in the case of the phosphorescent material depend on a magnitude of polarity of ambient host material molecules, ambient temperature, presence state of the material (e.g., solid state or liquid state), etc. Accordingly, different from the fluorescent material, it is generally difficult to expect the resultant EL characteristics for the phosphorescent material by simply removing a part of characteristics from photoluminescence results.

As a result of our investigation on various phosphorescence metal coordination compounds (including the metal coordination compound of formula (1)), we have found that a high-efficiency luminescence can be achieved in the case where a metal coordination compound has a molecular causing intramolecular rotation and exhibits a peak emission wavelength of at least 550 nm.

The intramolecular rotation is a phenomenon such that atomic groups disposed opposite to each other via a single bond (as a rotation axis) in molecule are rotated relative to each other. More specifically, in the molecular structure of the metal coordination compound of formula (1), the cyclic group CyN containing nitrogen atom and the cyclic group CyC containing carbon atom are bonded to each other via covalent bond, so that the covalent bond can function as an intramolecular rotation axis for the cyclic groups CyN and CyC. However, the intramolecular rotation between the cyclic groups CyN and CyC is suppressed by two connections between the nitrogen atom of CyN and the center metal M and between the carbon atom of CyC and the center metal M. Accordingly, herein, the intramolecular rotation of ligand means a rotation on a single bond (as intramolecular rotation axis) between a ring structure of CyN and a substituent therefor or on a single bond between a ring structure of CyC and a substituent therefor. Accordingly, a high-efficiency luminescence may be attributable to suppression of intramolecular rotation of ligand leading to a decrease in quenching path within molecule caused by the intramolecular rotation at the time of luminescence of metal coordination compound.

Further, as a result of our investigation on ligands of various phosphorescence metal coordination compounds regarding a relationship between a luminescence efficiency and a dipole moment calculated based on a semi-empirical molecular orbital method (AM1), we have found that a high-efficiency luminescence is achieved in the case where a metal coordination compound contains a ligand having a dipole moment of at most 7 debye, preferably at most 4 debye, and exhibits a peak emission wavelength of at least 550 nm.

This may be attributable to suppression of localization of electric charges of ligands, thus suppressing intermolecular interactions, e.g., between metal coordination compound molecules and between a guest material molecule (e.g., molecule of the metal coordination compound of formula (1)) and a host material molecule (e.g., molecule of CBP used in Examples described later) thereby to decrease the quenching path between their molecules to improve a luminescence efficiency.

Further, the magnitude of dipole moment of ligand is a factor for determining a lowest excited state affecting a degree of luminescence efficiency. The lowest excited state includes the above-mentioned MLCT* (metal-ligand charge transfer) state and ππ* state. In many cases, the MLCT* state provides a relatively high phosphorescence efficiency luminescence efficiency). This may be attributable to such a phenomenon that the metal M as a heavy atom directly affects a resultant luminescence state, thus effectively causing spin-orbit interaction to increase a resultant phosphorescence efficiency. When a ligand has a larger dipole moment, an excitation from a site having a larger (electric) charge distribution within the ligand to a site having a smaller charge distribution becomes advantageous. In other word, the ππ* excited state is stabilized to be disadvantageous to improvement in phosphorescence efficiency as described above.

The luminescence device (EL) device according to the present invention employs the above-mentioned metal coordination compound in an organic (compound) layer, particularly a luminescence layer.

Specifically, the luminescence device may preferably include the organic layer comprising the metal coordination compound between a pair of oppositely disposed electrodes comprising a transparent electrode (anode) and a metal electrode (cathode) which are supplied with a voltage to cause luminescence, thus constituting an electric-field luminescence device.

Figure 1B:
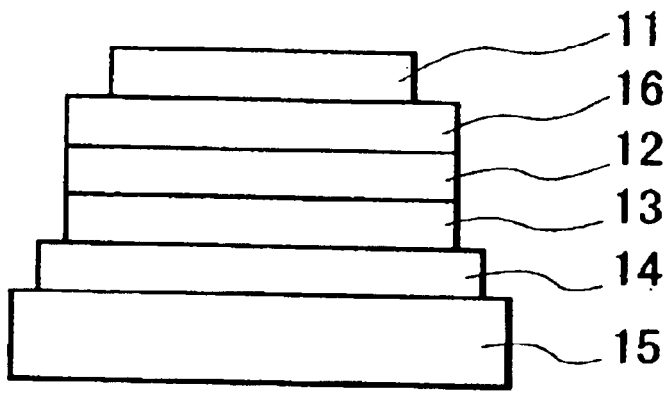
Figure 1C:
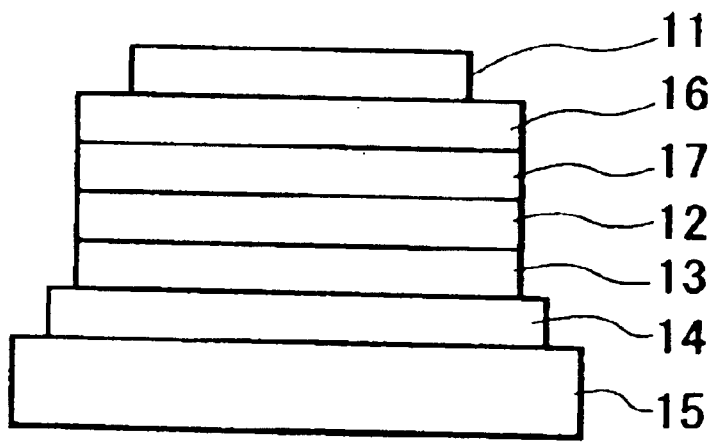

The luminescence device of the present invention has a layer structure shown in FIGS. 1A to 1C as specifically described above.

By the use of the metal coordination compound of formula (1) of the present invention, the resultant luminescence device has a high luminescence efficiency as described above.

The luminescence device according to the present invention may be applicable to devices required to allow energy saving and high luminance, such as those for display apparatus and illumination apparatus, a light source for printers, and backlight (unit) for a liquid crystal display apparatus. Specifically, in the case of using the luminescence device of the present invention in the display apparatus, it is possible to provide a flat panel display apparatus capable of exhibiting an excellent energy saving performance, a high visibility and a good lightweight property. With respect to the light source, it becomes possible to replace a laser light source of laser beam printer currently used widely with the luminescence device according to the present invention. Further, when the luminescence device of the present invention is arranged in independently addressable arrays as an exposure means for effecting desired exposure of light to a photosensitive drum for forming an image, it becomes possible to considerably reducing the volume (size) of image forming apparatus. With respect to the illumination apparatus and backlight (unit), the resultant apparatus (unit) using the luminescence device of the present invention is expected to have an energy saving effect.

Hereinbelow, the metal coordination compound of formula (1) used in the luminescence device of the present invention will be described more specifically.

Specific and non-exhaustive examples of the metal coordination compound of formula (1) may include those (Example Compound Nos. 1–205) shown in Tables 1–9.

In Tables 1–9, abbreviations for respective cyclic groups (CyN and CyC) represent groups shown below.

Ph: 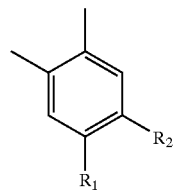

Tn1: 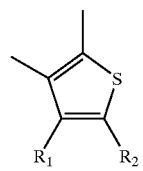

Tn2: 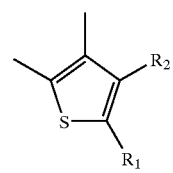

Tn3: 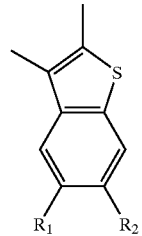

Np: 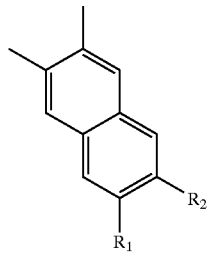

Qn:1 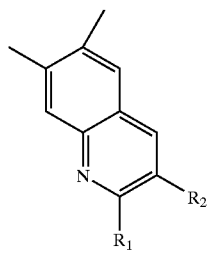

Qn2:
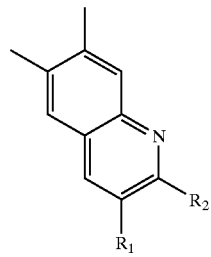

Qx:
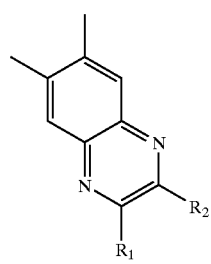

Qz1:
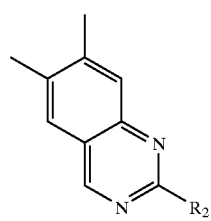

Qz2:
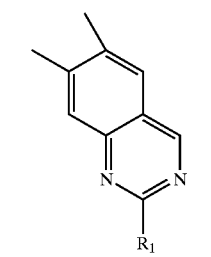

Cn1:
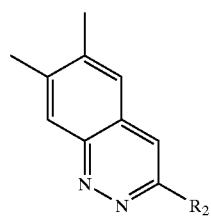

Cn2:
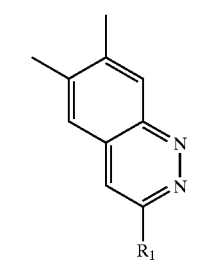

Pz:
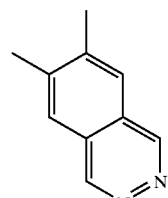

Pr:
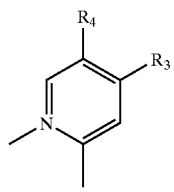

Pd:
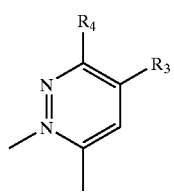

Py1:
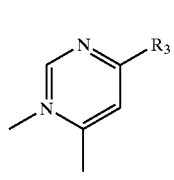

Pa:
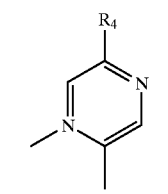

Py2:
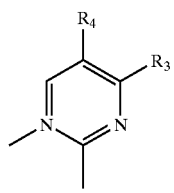

Pz:
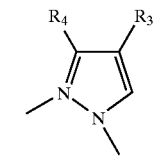

In the above structural formulas (Ph to Pz), an unconnected covalent (single) linkage extended in an upper-left direction or a lower-left direction is a linkage connected to the center metal M, and the other unconnected covalent linkage extended in an upper direction or a lower direction is a linkage connected to an adjacent cyclic group.

TABLE 1

| No | M | n | CyN | CyC | R1 | R2 | R3 | R4 |
|----|----|----|-----|-----|----|----|----|----|
| 1 | Ir | 3 | Pr | Tn1 | H | H | H | H |
| 2 | Ir | 3 | Pr | Tn2 | H | H | H | H |
| 3 | Ir | 3 | Pr | Tn3 | H | H | H | H |
| 4 | Ir | 3 | Pr | Qn1 | H | H | H | H |
| 5 | Ir | 3 | Pr | Qn2 | H | H | H | H |
| 6 | Ir | 3 | Pr | Qx | H | H | H | H |
| 7 | Ir | 3 | Pr | Qz1 | — | H | H | H |
| 8 | Ir | 3 | Pr | Qz2 | H | — | H | H |
| 9 | Ir | 3 | Pr | Cn1 | — | H | H | H |
| 10 | Ir | 3 | Pr | Cn2 | H | — | H | H |
| 11 | Ir | 3 | Pr | Pz | — | — | H | H |
| 12 | Ir | 3 | Pd | Ph | H | H | H | H |
| 13 | Ir | 3 | Pd | Tn1 | H | H | H | H |
| 14 | Ir | 3 | Pd | Tn2 | H | H | H | H |
| 15 | Ir | 3 | Pd | Tn3 | H | H | H | H |
| 16 | Ir | 3 | Pd | Np | H | H | H | H |
| 17 | Ir | 3 | Pd | Qn1 | H | H | H | H |
| 18 | Ir | 3 | Pd | Qn2 | H | H | H | H |
| 19 | Ir | 3 | Pd | Qx | H | H | H | H |
| 20 | Ir | 3 | Pd | Qz1 | — | H | H | H |
| 21 | Ir | 3 | Pd | Qz2 | H | — | H | H |
| 22 | Ir | 3 | Pd | Cn1 | — | H | H | H |
| 23 | Ir | 3 | Pd | Cn2 | H | — | H | H |
| 24 | Ir | 3 | Pd | Pz | — | — | H | H |
| 25 | Ir | 3 | Py1 | Ph | H | H | H | — |

TABLE 2

| No | M | n | CyN | CyC | R1 | R2 | R3 | R4 |
|----|----|----|-----|-----|----|----|----|----|
| 26 | Ir | 3 | Py1 | Tn1 | H | H | H | — |
| 27 | Ir | 3 | Py1 | Tn2 | H | H | H | — |
| 28 | Ir | 3 | Py1 | Tn3 | H | H | H | — |
| 29 | Ir | 3 | Py1 | Np | H | H | H | — |
| 30 | Ir | 3 | Py1 | Qn1 | H | H | H | — |
| 31 | Ir | 3 | Py1 | Qn2 | H | H | H | — |
| 32 | Ir | 3 | Pa | Ph | H | H | — | H |
| 33 | Ir | 3 | Pa | Tn1 | H | H | — | H |
| 34 | Ir | 3 | Pa | Tn2 | H | H | — | H |
| 35 | Ir | 3 | Pa | Np | H | H | — | H |
| 36 | Ir | 3 | Pa | Qn1 | H | H | — | H |
| 37 | Ir | 3 | Pa | Qn2 | H | H | — | H |
| 38 | Ir | 3 | Py2 | Ph | H | H | H | H |
| 39 | Ir | 3 | Py2 | Tn1 | H | H | H | H |
| 40 | Ir | 3 | Py2 | Tn2 | H | H | H | H |
| 41 | Ir | 3 | Py2 | Tn3 | H | H | H | H |
| 42 | Ir | 3 | Py2 | Np | H | H | H | H |
| 43 | Ir | 3 | Py2 | Qn1 | H | H | H | H |
| 44 | Ir | 3 | Py2 | Qn2 | H | H | H | H |
| 45 | Ir | 3 | Pz | Ph | H | H | H | H |
| 46 | Ir | 3 | Pz | Tn1 | H | H | H | H |
| 47 | Ir | 3 | Pz | Tn2 | H | H | H | H |
| 48 | Ir | 3 | Pz | Np | H | H | H | H |
| 49 | Ir | 3 | Pz | Qn1 | H | H | H | H |
| 50 | Ir | 3 | Pz | Qn2 | H | H | H | H |

TABLE 3

| No | M | n | CyN | CyC | R1 | R2 | R3 | R4 |
|----|----|----|-----|-----|----|----|----|----|
| 51 | Rh | 3 | Pr | Tn1 | H | H | H | H |
| 52 | Rh | 3 | Pr | Tn2 | H | H | H | H |
| 53 | Rh | 3 | Pr | Tn3 | H | H | H | H |
| 54 | Rh | 3 | Pr | Qn1 | H | H | H | H |
| 55 | Rh | 3 | Pr | Qn2 | H | H | H | H |
| 56 | Rh | 3 | Pr | Qx | H | H | H | H |
| 57 | Rh | 3 | Pr | Qz1 | — | H | H | H |
| 58 | Rh | 3 | Pr | Qz2 | H | — | H | H |
| 59 | Rh | 3 | Pr | Cn1 | — | H | H | H |
| 60 | Rh | 3 | Pr | Cn2 | H | — | H | H |
| 61 | Rh | 3 | Pr | Pz | — | — | H | H |
| 62 | Rh | 3 | Pd | Ph | H | H | H | H |
| 63 | Rh | 3 | Pd | Tn1 | H | H | H | H |
| 64 | Rh | 3 | Pd | Tn2 | H | H | H | H |
| 65 | Rh | 3 | Pd | Tn3 | H | H | H | H |
| 66 | Rh | 3 | Pd | Np | H | H | H | H |
| 67 | Rh | 3 | Pd | Qn1 | H | H | H | H |
| 68 | Rh | 3 | Pd | Qn2 | H | H | H | H |
| 69 | Rh | 3 | Pd | Qx | H | H | H | H |
| 70 | Rh | 3 | Pd | Qz1 | — | H | H | H |
| 71 | Rh | 3 | Pd | Qz2 | H | — | H | H |
| 72 | Rh | 3 | Pd | Cn1 | — | H | H | H |
| 73 | Rh | 3 | Pd | Cn2 | H | — | H | H |
| 74 | Rh | 3 | Pd | Pz | — | — | H | H |
| 75 | Rh | 3 | Py1 | Ph | H | H | H | — |

TABLE 4

| No | M | n | CyN | CyC | R1 | R2 | R3 | R4 |
|----|----|----|-----|-----|----|----|----|----|
| 76 | Rh | 3 | Py1 | Tn1 | H | H | H | — |
| 77 | Rh | 3 | Py1 | Tn2 | H | H | H | — |
| 78 | Rh | 3 | Py1 | Tn3 | H | H | H | — |
| 79 | Rh | 3 | Py1 | Np | H | H | H | — |
| 80 | Rh | 3 | Py1 | Qn1 | H | H | H | — |
| 81 | Rh | 3 | Py1 | Qn2 | H | H | H | — |
| 82 | Rh | 3 | Pa | Ph | H | H | — | H |
| 83 | Rh | 3 | Pa | Tn1 | H | H | — | H |
| 84 | Rh | 3 | Pa | Tn2 | H | H | — | H |
| 85 | Rh | 3 | Pa | Np | H | H | — | H |
| 86 | Rh | 3 | Pa | Qn1 | H | H | — | H |
| 87 | Rh | 3 | Pa | Qn2 | H | H | — | H |
| 88 | Rh | 3 | Py2 | Ph | H | H | H | H |
| 89 | Rh | 3 | Py2 | Tn1 | H | H | H | H |
| 90 | Rh | 3 | Py2 | Tn2 | H | H | H | H |
| 91 | Rh | 3 | Py2 | Tn3 | H | H | H | H |
| 92 | Rh | 3 | Py2 | Np | H | H | H | H |
| 93 | Rh | 3 | Py2 | Qn1 | H | H | H | H |
| 94 | Rh | 3 | Py2 | Qn2 | H | H | H | H |
| 95 | Rh | 3 | Pz | Ph | H | H | H | H |
| 96 | Rh | 3 | Pz | Tn1 | H | H | H | H |
| 97 | Rh | 3 | Pz | Tn2 | H | H | H | H |
| 98 | Rh | 3 | Pz | Np | H | H | H | H |
| 99 | Rh | 3 | Pz | Qn1 | H | H | H | H |
| 100 | Rh | 3 | Pz | Qn2 | H | H | H | H |

TABLE 5

| No | M | n | CyN | CyC | R1 | R2 | R3 | R4 |
|----|----|----|-----|-----|----|----|----|----|
| 101 | Pd | 2 | Pr | Tn1 | H | H | H | H |
| 102 | Pd | 2 | Pr | Tn2 | H | H | H | H |
| 103 | Pd | 2 | Pr | Tn3 | H | H | H | H |
| 104 | Pd | 2 | Pr | Qn1 | H | H | H | H |
| 105 | Pd | 2 | Pr | Qn2 | H | H | H | H |
| 106 | Pd | 2 | Pr | Qx | H | H | H | H |
| 107 | Pd | 2 | Pr | Qz1 | — | H | H | H |
| 108 | Pd | 2 | Pr | Qz2 | H | — | H | H |
| 109 | Pd | 2 | Pr | Cn1 | — | H | H | H |
| 110 | Pd | 2 | Pr | Cn2 | H | — | H | H |
| 111 | Pd | 2 | Pr | Pz | — | — | H | H |
| 112 | Pd | 2 | Pd | Ph | H | H | H | H |
| 113 | Pd | 2 | Pd | Tn1 | H | H | H | H |
| 114 | Pd | 2 | Pd | Tn2 | H | H | H | H |
| 115 | Pd | 2 | Pd | Tn3 | H | H | H | H |
| 116 | Pd | 2 | Pd | Np | H | H | H | H |
| 117 | Pd | 2 | Pd | Qn1 | H | H | H | H |
| 118 | Pd | 2 | Pd | Qn2 | H | H | H | H |
| 119 | Pd | 2 | Pd | Qx | H | H | H | H |
| 120 | Pd | 2 | Pd | Qz1 | — | H | H | H |
| 121 | Pd | 2 | Pd | Qz2 | H | — | H | H |
| 122 | Pd | 2 | Pd | Cn1 | — | H | H | H |
| 123 | Pd | 2 | Pd | Cn2 | H | — | H | H |
| 124 | Pd | 2 | Pd | Pz | — | — | H | H |
| 125 | Pd | 2 | Py1 | Ph | H | H | H | — |

TABLE 6

| No | M | n | CyN | CyC | R1 | R2 | R3 | R4 |
|---|---|---|---|---|---|---|---|---|
| 126 | Pd | 2 | Py1 | Tn1 | H | H | H | — |
| 127 | Pd | 2 | Py1 | Tn2 | H | H | H | — |
| 128 | Pd | 2 | Py1 | Tn3 | H | H | H | — |
| 129 | Pd | 2 | Py1 | Np | H | H | H | — |
| 130 | Pd | 2 | Py1 | Qn1 | H | H | H | — |
| 131 | Pd | 2 | Py1 | Qn2 | H | H | H | — |
| 132 | Pd | 2 | Pa | Ph | H | H | — | H |
| 133 | Pd | 2 | Pa | Tn1 | H | H | — | H |
| 134 | Pd | 2 | Pa | Tn2 | H | H | — | H |
| 135 | Pd | 2 | Pa | Np | H | H | — | H |
| 136 | Pd | 2 | Pa | Qn1 | H | H | — | H |
| 137 | Pd | 2 | Pa | Qn2 | H | H | — | H |
| 138 | Pd | 2 | Py2 | Ph | H | H | H | H |
| 139 | Pd | 2 | Py2 | Tn1 | H | H | H | H |
| 140 | Pd | 2 | Py2 | Tn2 | H | H | H | H |
| 141 | Pd | 2 | Py2 | Tn3 | H | H | H | H |
| 142 | Pd | 2 | Py2 | Np | H | H | H | H |
| 143 | Pd | 2 | Py2 | Qn1 | H | H | H | H |
| 144 | Pd | 2 | Py2 | Qn2 | H | H | H | H |
| 145 | Pd | 2 | Pz | Ph | H | H | H | H |
| 146 | Pd | 2 | Pz | Tn1 | H | H | H | H |
| 147 | Pd | 2 | Pz | Tn2 | H | H | H | H |
| 148 | Pd | 2 | Pz | Np | H | H | H | H |
| 149 | Pd | 2 | Pz | Qn1 | H | H | H | H |
| 150 | Pd | 2 | Pz | Qn2 | H | H | H | H |

TABLE 7

| No | M | n | CyN | CyC | R1 | R2 | R3 | R4 |
|---|---|---|---|---|---|---|---|---|
| 151 | Ir | 3 | Pr | Tn1 | H | Si(CH$_2$)$_3$ | H | H |
| 152 | Ir | 3 | Pr | Tn1 | H | SC$_2$H$_5$ | H | H |
| 153 | Ir | 3 | Pr | Tn1 | H | OCH$_3$ | H | H |
| 154 | Ir | 3 | Pr | Tn1 | H | H | H | F |
| 155 | Ir | 3 | Pr | Tn1 | H | H | F | F |
| 156 | Ir | 3 | Pr | Tn1 | H | H | H | C$_5$H$_{11}$ |
| 157 | Ir | 3 | Pr | Tn1 | H | H | H | OCH$_3$ |
| 158 | Ir | 3 | Pr | Tn1 | H | H | OC$_4$H$_9$ | H |
| 159 | Ir | 3 | Pr | Tn1 | H | H | H | OCF$_3$ |
| 160 | Ir | 3 | Pr | Tn1 | H | H | H | SC$_2$H$_5$ |
| 161 | Ir | 3 | Pr | Tn1 | H | H | H | COC$_2$H$_5$ |
| 162 | Ir | 3 | Pr | Tn1 | H | H | H | COOC$_2$H$_5$ |
| 163 | Ir | 3 | Pr | Tn1 | H | H | H | OCOC$_2$H$_5$ |
| 164 | Ir | 3 | Py1 | Np | H | F | H | — |
| 165 | Ir | 3 | Pa | Np | H | OCH$_3$ | — | H |
| 166 | Ir | 3 | Pz | Ph | H | H | H | CH$_3$ |
| 167 | Ir | 3 | Pd | Ph | H | NO$_2$ | H | H |
| 168 | Ir | 3 | Py1 | Ph | H | NO$_2$ | H | — |
| 169 | Ir | 3 | Pa | Ph | H | NO$_2$ | — | H |
| 170 | Ir | 3 | Py2 | Ph | H | F | H | H |
| 171 | Ir | 3 | Pz | Ph | H | F | H | H |
| 172 | Ir | 3 | Pz | Ph | H | CH$_2$CH=CHCH$_2$CH$_3$ | H | H |
| 173 | Ir | 3 | Pz | Ph | H | CH$_2$C≡CCH$_2$CH$_3$ | H | H |
| 174 | Rh | 3 | Pr | Tn1 | H | Si(CH$_2$)$_3$ | H | H |
| 175 | Rh | 3 | Pr | Tn1 | H | OCH$_3$ | H | H |

TABLE 8

| No | M | n | CyN | CyC | R1 | R2 | R3 | R4 |
|---|---|---|---|---|---|---|---|---|
| 176 | Rh | 3 | Pr | Tn1 | H | H | H | F |
| 177 | Rh | 3 | Pr | Tn1 | H | F | F | F |
| 178 | Rh | 3 | Pr | Tn1 | H | H | H | C$_5$H$_{11}$ |
| 179 | Rh | 3 | Pr | Tn1 | H | H | H | OCH$_3$ |
| 180 | Rh | 3 | Pr | Tn1 | H | H | OC$_4$H$_9$ | H |
| 181 | Rh | 3 | Pr | Tn1 | H | H | H | OCF$_3$ |
| 182 | Rh | 3 | Pr | Tn1 | H | H | H | SC$_2$H$_5$ |
| 183 | Rh | 3 | Pr | Tn1 | H | H | H | COC$_2$H$_5$ |
| 184 | Rh | 3 | Py1 | Np | H | F | H | — |
| 185 | Rh | 3 | Pa | Np | H | OCH$_3$ | — | H |
| 186 | Rh | 3 | Pz | Ph | H | H | H | CH$_3$ |
| 187 | Rh | 3 | Pz | Tn1 | H | F | H | H |
| 188 | Pd | 2 | Pr | Tn1 | H | Si(CH$_2$)$_3$ | H | H |
| 189 | Pd | 2 | Pr | Tn1 | H | OCH$_3$ | H | H |
| 190 | Pd | 2 | Pr | Tn1 | H | H | H | F |
| 191 | Pd | 2 | Pr | Tn1 | H | H | F | F |
| 192 | Pd | 2 | Pr | Tn1 | H | H | H | C$_5$H$_{11}$ |
| 193 | Pd | 2 | Pr | Tn1 | H | H | H | OCH$_3$ |
| 194 | Pd | 2 | Pr | Tn1 | H | H | OC$_4$H$_9$ | H |
| 195 | Pd | 2 | Pr | Tn1 | H | H | H | OCF$_3$ |
| 196 | Pd | 2 | Pr | Tn1 | H | H | H | SC$_2$H$_5$ |
| 197 | Pd | 2 | Pr | Tn1 | H | H | H | COC$_2$H$_5$ |
| 198 | Pd | 2 | Py1 | Np | H | F | H | — |
| 199 | Pd | 2 | Pa | Np | H | OCH$_3$ | — | H |
| 200 | Pd | 2 | Pz | Ph | H | H | H | CH$_3$ |
| 201 | Pd | 2 | Pz | Tn1 | H | F | H | H |

TABLE 9

| No | M | n | CyN | CyC | R1 | R2 | R3 | R4 |
|---|---|---|---|---|---|---|---|---|
| 202 | Ir | 3 | Pr | Tn1 | H | H | H | CF$_3$ |
| 203 | Ir | 3 | Pr | Tn1 | H | CH$_3$ | H | H |
| 204 | Ir | 3 | Pr | Tn1 | H | H | CF$_3$ | H |
| 205 | Ir | 3 | Pr | Tn3 | H | H | H | CF$_3$ |

Hereinbelow, the present invention will be described more specifically based on Examples with reference to the drawing.

EXAMPLES 1–10

In these examples, the following metal coordination compounds 1–10 were used in respective luminescence layers for Examples 1–10, respectively.

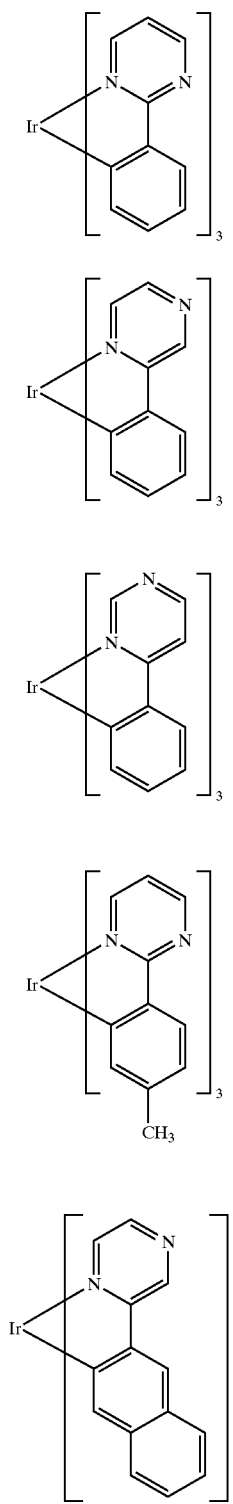

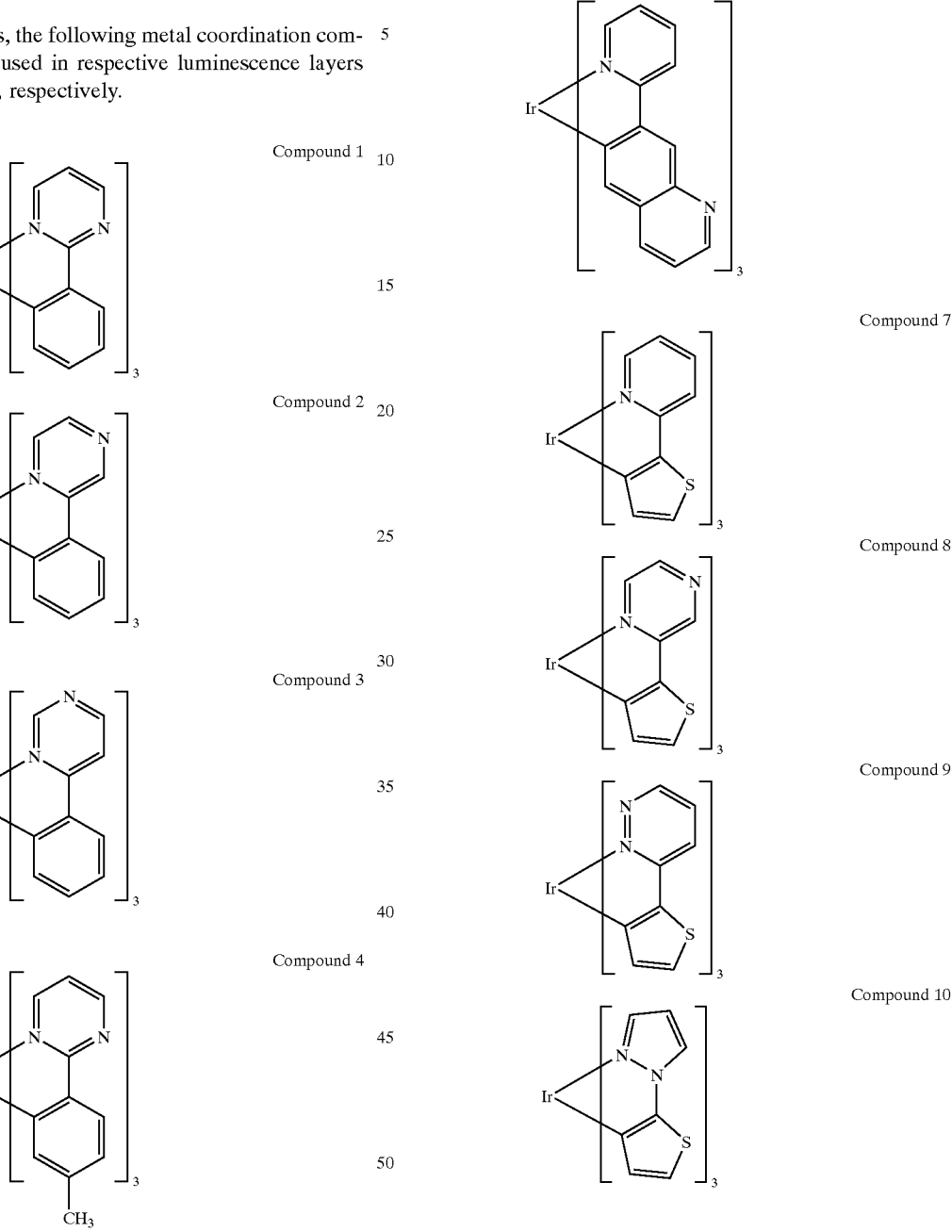

Each of luminescence devices having a structure shown in FIG. 1B were prepared in the following manner.

On a glass substrate (transparent substrate 15), a 100 nm-thick film (transparent electrode 14) of ITO (indium tin oxide) was formed by sputtering, followed by patterning to have an (opposing) electrode area of 3 mm$^2$.

On the ITO-formed substrate, three organic layers and two metal electrode layers shown below were successively formed by vacuum (vapor) deposition using resistance heating in a vacuum chamber ($10^{-4}$ Pa).

Organic layer 1 (hole transport layer 13) (40 nm): α-NPD
Organic layer 2 (luminescence layer 12) (20 nm): mixture of CBP:metal complex (metal coordination compound) (95:5 by weight)

Organic layer 3 (electron transport layer 16) (30 nm): Alq3

Metal electrode layer 1 (metal electrode 11) (15 nm): Al—Li alloy (Li=1.8 wt. %)

Metal electrode layer 2 (metal electrode 11) (100 nm): Al

Each of the thus-prepared luminescence devices was taken out of the vacuum chamber and was subjected to a continuous energization test in an atmosphere of dry nitrogen gas stream so as to remove device deterioration factors, such as oxygen and moisture (water content).

The continuous energization test was performed by continuously applying a voltage at a constant current density of 70 mA/cm$^2$ to the luminescence device having the ITO (transparent) electrode (as an anode) and the Al (metal) electrode (as a cathode), followed by measurement of luminance (brightness) with time so as to determine a time (luminance half-life) required for decreasing an initial luminance (80–240 cd/m$^2$) to ½ thereof.

The results are shown in Table 10 appearing hereinafter.

COMPARATIVE EXAMPLE 1

A comparative luminescence device was prepared and evaluated in the same manner as in Examples 1–10 except that the Ir coordination compound (metal coordination compounds 1–10) was changed to Ir-phenylpyridine complex (Ir(ppy)$_3$) shown below.

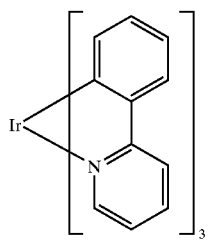

The results are shown in Table 10 below.

TABLE 10

| Ex. No. | Compound No. | Luminance half-life (Hr) |
| --- | --- | --- |
| Ex. 1 | 1 | 550 |
| Ex. 2 | 2 | 900 |
| Ex. 3 | 3 | 600 |
| Ex. 4 | 4 | 650 |
| Ex. 5 | 5 | 950 |
| Ex. 6 | 6 | 800 |
| Ex. 7 | 7 | 850 |
| Ex. 8 | 8 | 600 |
| Ex. 9 | 9 | 750 |
| Ex. 10 | 10 | 900 |
| Comp. Ex. 1 | Ir(ppy)$_3$ | 350 |

As is apparent from Table 10, compared with the conventional luminescence device using Ir(ppy)$_3$, the luminescence devices using the metal coordination compounds of formula (1) according to the present invention provide longer luminance half-lifes, thus resulting in an EL device having a high durability (luminance stability) based on a good stability of the metal coordination compound of formula (1) of the present invention.

EXAMPLES 11–16

In these examples, metal coordination compounds of formula (1) (Compounds 11–16) were used in respective luminescence layers for Examples 11–16, respectively.

Compound 11

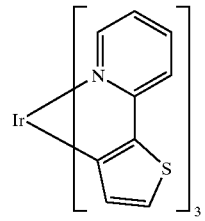

Compound 12

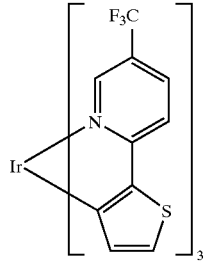

Compound 13

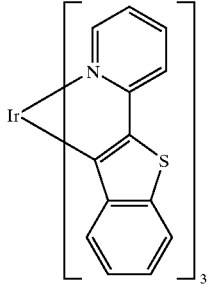

Compound 14

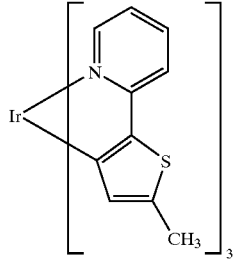

Compound 15

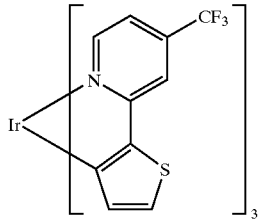

-continued

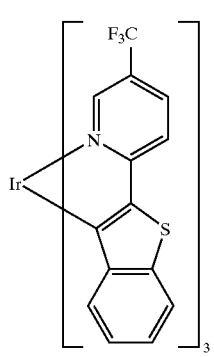

Compound 16

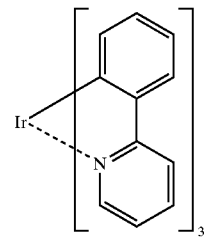

Each of luminescence devices having a structure shown in FIG. 1C were prepared in the following manner.

On a glass substrate (transparent substrate 15), a 100 nm-thick film (transparent electrode 14) of ITO (indium tin oxide) was formed by sputtering, followed by patterning to have an (opposing) electrode area of 3 mm².

On the ITO-formed substrate, three organic layers and two metal electrode layers shown below were successively formed by vacuum (vapor) deposition using resistance heating in a vacuum chamber ($10^{-4}$ Pa).

Organic layer 1 (hole transport layer 13) (40 nm): α-NPD

Organic layer 2 (luminescence layer 12) (20 nm): mixture of CBP: metal coordination compound of formula (1) (93:7 by weight)

Organic layer 3 (exciton diffusion prevention layer 17) (10 nm): BCP

Organic layer 4 (electron transport layer 16) (30 nm): Alq3

Metal electrode layer 1 (metal electrode 11) (15 nm): Al—Li alloy (Li=1.8 wt. %)

Metal electrode layer 2 (metal electrode 11) (100 nm): Al

EL characteristics of the luminescence devices using the metal coordination compounds of formula (1) (Compounds 11–16) were measured by using a microammeter ("Model 4140B", mfd. by Hewlett-Packard Co.) for a current density under application of a voltage of 12 volts (current-voltage characteristic), using a spectrophotofluoro-meter ("Model SR1", mfd. by Topcon K.K.) for a peak emission wavelength $\lambda_{PE}$ (luminescence spectrum), and using a luminance meter ("Model BM7", mfd. by Topcon K.K.) for a luminescence efficiency (luminescence luminance). Further, an energy conversion efficiency was obtained according to the following equation:

Energy conversion efficiency $(lm/W)=(\pi \times$luminescence efficiency $(cd/A))$/applied voltage (V).

All the above-prepared luminescence devices showed a good rectification characteristic.

The results are shown in Table 11.

COMPARATIVE EXAMPLE 2

A comparative luminescence device was prepared and evaluated in the same manner as in Examples 11–16 except that the metal coordination compound of formula (1) was changed to Ir-phenylpyridine complex (Ir(ppy)₃) shown below.

The results are shown in Table 11 below.

TABLE 11

| Ex. No | Ex. Comp. No. | λPE (nm) | Energy conversion efficiency (lm/W) | Luminescence efficiency (cd/A) | Current density (mA/cm² at 12 V) | Luminance half-life (Hr) |
|---|---|---|---|---|---|---|
| Ex. 11 | 11 | 552 | 0.9 | 6.3 | 100 | 300 |
| Ex. 12 | 12 | 565 | 1.0 | 4.0 | 215 | 350 |
| Ex. 13 | 13 | 600 | 2.9 | 3.1 | 125 | 250 |
| Ex. 14 | 14 | 560 | 1.2 | 5.7 | 30 | 300 |
| Ex. 15 | 15 | 575 | 1.4 | 5.5 | 110 | 320 |
| Ex. 16 | 16 | 620 | 0.5 | 0.6 | 260 | 300 |
| Comp. Ex. 2 | Ir(ppy)₃ | 510 | 6.0 | 19.0 | 20 | 150 |

As shown in Table 11, compared with the luminescence device using Ir(ppy)₃ (Comparative Example 2) showing $\lambda_{PE}$=510 nm, the luminescence devices using the metal coordination compound of formula (1) according to the present invention showed longer peak emission wavelengths ($\lambda_{PE}$=552–620 nm) by ca. 40–110 nm.

When the peak emission wavelength was shifted to the longer wavelength side, a probability of thermal quenching of energy is generally increased to lower a resultant luminescence efficiency based on the energy gap low. The lower luminescence efficiencies (0.6–6.3 cd/A) of the luminescence devices of the present invention compared with that (19.0 cd/A) of the luminescence device using Ir(ppy)₃ may be attributable to the above phenomenon.

According to the energy gap law, it is said that it is generally difficult to increase energy conversion efficiencies of luminescence devices using luminescent materials for longer wavelength-light (yellowish green to red). However, the luminescence devices using the metal coordination compounds of the present invention exhibits practically sufficient energy conversion efficiencies of at least 0.5 lm/W.

As apparent from the results of the luminance half-lifes of the luminescence devices in Table 11, compared with the luminescence device using Ir(ppy)₃ showing the luminance half-life of 150 hours, the luminescence devices using the metal coordination compounds of formula (1) according to the present invention showed considerably longer luminance half-lifes of 250–350 hours.

Based on the results shown in Table 11, luminescence efficiencies of the luminescence devices using Compounds 11–16 according to the present invention were compared in order to evaluate the effect of presence of a portion causing intramolecular rotation by classifying Compounds 11–16 into two groups having closer structures and peak emission wavelengths (Compounds 11, 12, 14 and 15 having peak emission wavelengths of 552–575 nm and Compounds 13 and 16 having peak emission wavelengths of 600–620 nm).

The luminescence device using Compound 11 exhibited a luminescence efficiency (6.3 cd/A) relatively larger than those (4.0–5.7 cd/A) of the luminescence devices using Compounds 12, 14 and 15 having the same molecular skeleton as Compound 11. This may be attributable to a difference in ligand structure. Specifically, the ligand of Compound 11 is free from a portion causing intramolecular rotation but those of Compounds 12, 14 and 15 have a portion (substituent) causing intramolecular rotation via a single bond.

Similarly, the luminescence device using Compound 13 (free from a portion causing intramolecular rotation) exhibited a luminescence efficiency (3.1 cd/A) relatively larger than that (0.6 cd/A) of the luminescence device using Compound 16 (having a portion causing intramolecular rotation).

Further, the luminescence devices using Compounds 11–16 exhibited the peak emission wavelengths of at least 550 nm.

Accordingly, it was substantiated that the metal coordination compound of formula (1) provided better luminescence efficiencies when it had a molecular structure free from a portion causing intramolecular rotation and exhibited a peak emission wavelength of at least 550 nm.

EXAMPLE 17

Synthesis of Compound 11

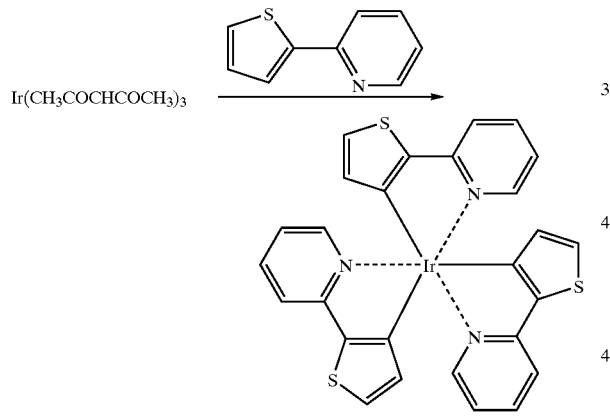

In a 200 ml-four necked flask, 100 ml of glycerol was placed and heat-stirred for 2 hours at 130–140° C. while supplying nitrogen gas therein in the form of bubbles, followed by cooing to 100° C. by standing. To glycerol, 1.94 g (12.00 mM) of 2-(2-thienyl)pyridine and 1.00 g (2.0 mM) of Iridium (III) acetylacetonate were added, followed by heat-refluxing for 8 hours under stirring in nitrogen gas stream.

After the reaction, the reaction mixture was cooled to room temperature and poured into 600 ml of 1N—HCl. The resultant precipitate was recovered by filtration and washed with water, followed by drying for 4 hours at 100° C. under reduced pressure and purification by silica gel column chromatography (eluent: chloroform) to obtain 0.38 g of Iridium (III) tris[2-(2-thienylphenyl)pyridine) (red powder) (Yield: 28.2%).

EXAMPLE 18

Synthesis of Compound 12

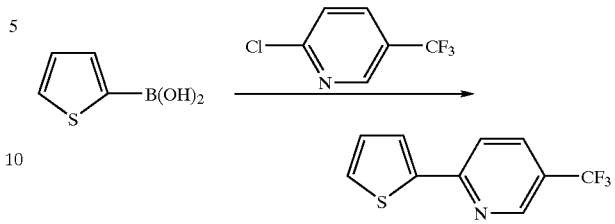

In a 1 liter-three necked flask, 33.70 g (185.8 mM) of 2-chloro-5-trifluoromethylpyridine, 23.77 g (185.8 mM) of thiophene-2-bronic acid, 200 ml of toluene, 100 ml of ethanol and 200 ml of 2M-sodium carbonate aqueous solution were placed and stirred in a nitrogen gas stream at room temperature. Under stirring, to the mixture, 6.66 g (5.76 mM) of tetrakis (triphenylphosphine) palladium (0) was added, followed by heat-refluxing for 5 hours under stirring in nitrogen gas stream.

After the reaction, the reaction mixture was cooled, followed by extraction with cool water and toluene. The organic layer was washed with water until the system showed neutral, followed by distilling off of the solvent under reduced pressure to obtain a residue. The residue was purified by silica gel column chromatography (eluent: toluene/hexane=2/1) and recrystallized from ethanol to obtain a pale yellow crystal. The crystal was purified by alumina column chromatography (eluent: toluene) and recrystallized from ethanol to obtain 20.3 g of 2-(5-trifluoromethylpyridine-2-yl)thiophene (Yield: 47.6%).

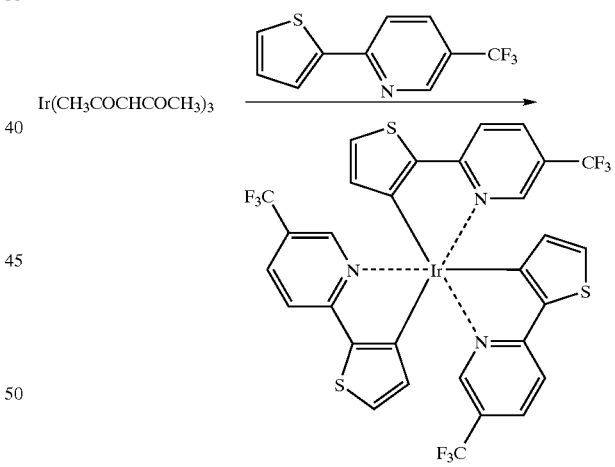

In a 200 ml-four necked flask, 100 ml of glycerol was placed and heat-stirred for 2 hours at 130–140° C. while supplying nitrogen gas therein in the form of bubbles, followed by cooing to 100° C. by standing. To glycerol, 2.74 g (12.0 mM) of 2-(5-trifluoromethylpyridine-2-yl)thiophene and 1.00 g (2.0 mM) of Iridium (III) acetylacetonate were added, followed by heat-refluxing for 8 hours under stirring in nitrogen gas stream.

After the reaction, the reaction mixture was cooled to room temperature and poured into 600 ml of 1N-HCl. The resultant precipitate was recovered by filtration and washed with water, followed by drying for 4 hours at 100° C. under reduced pressure and purification by silica gel column chromatography (eluent: chloroform) to obtain 0.35 g of Iridium (III) tris[2-(5-trifluoromethylpyridine-2-yl)thiophene] (red powder) (Yield: 20.0%).

EXAMPLE 19

Synthesis Compound 13

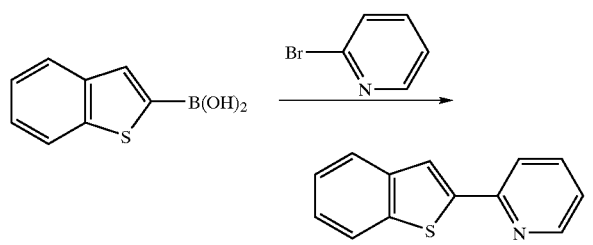

In a 1 liter-three necked flask, 26.6 g (168.5 mM) of 2-bromopyridine, 30.0 g (168.5 mM) of benzo[b]thiophene-2-bronic acid, 170 ml of toluene, 85 ml of ethanol and 170 ml of 2M-sodium carbonate aqueous solution were placed and stirred in a nitrogen gas stream at room temperature. Under stirring, to the mixture, 6.18 g (5.35 mM) of tetrakis(triphenyl-phosphine) palladium (0) was added, followed by heat-refluxing for 5 hours under stirring in nitrogen gas stream.

After the reaction, the reaction mixture was cooled, followed by extraction with cool water and toluene. The organic layer was washed with water until the system showed neutral, followed by distilling off of the solvent under reduced pressure to obtain a residue. The residue was purified by silica gel column chromatography (eluent: toluene/hexane=5/1) to obtain a colorless crystal. The crystal was purified by alumina column chromatography (eluent: toluene) and recrystallized from ethanol to obtain 12.6 g of 2-(pyridine-2-yl)benzo[b]thiophene (Yield: 35.4%).

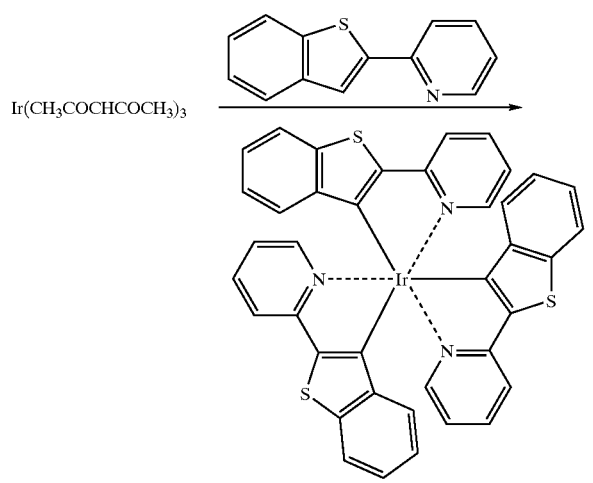

In a 200 ml-four necked flask, 100 ml of glycerol was placed and heat-stirred for 2 hours at 130–140° C. while supplying nitrogen gas therein in the form of bubbles, followed by cooing to 100° C. by standing. To glycerol, 2.52 g (12.0 mM) of 2-(pyridyl-2-yl)benzo[b]thiophene and 1.00 g (2.0 mM) of Iridium (III) acetylacetonate were added, followed by heat-refluxing for 8 hours under stirring in nitrogen gas stream.

After the reaction, the reaction mixture was cooled to room temperature and poured into 600 ml of 1N-HCl. The resultant precipitate was recovered by filtration, washed with water, and dissolved in acetone followed by removal of the insoluble matter by filtration and distilling-off of acetone under reduced pressure to obtain a residue. The residue was purified by silica gel column chromatography (eluent: chloroform) to obtain 0.38 g of Iridium (III) tris[2-(pyridine-2-yl)benzo[b]thiophene] (red powder) (Yield: 23.1%).

EXAMPLE 20

Synthesis Compound 14

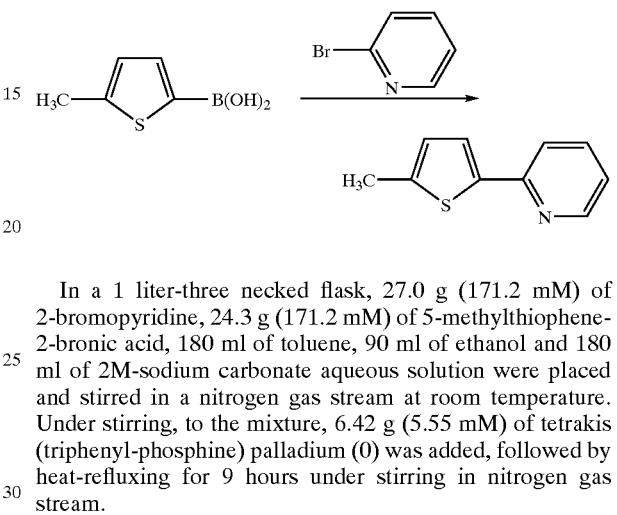

In a 1 liter-three necked flask, 27.0 g (171.2 mM) of 2-bromopyridine, 24.3 g (171.2 mM) of 5-methylthiophene-2-bronic acid, 180 ml of toluene, 90 ml of ethanol and 180 ml of 2M-sodium carbonate aqueous solution were placed and stirred in a nitrogen gas stream at room temperature. Under stirring, to the mixture, 6.42 g (5.55 mM) of tetrakis(triphenyl-phosphine) palladium (0) was added, followed by heat-refluxing for 9 hours under stirring in nitrogen gas stream.

After the reaction, the reaction mixture was cooled, followed by extraction with cool water and toluene. The organic layer was washed with water until the system showed neutral, followed by distilling off of the solvent under reduced pressure to obtain a residue. The residue was purified by silica gel column chromatography (eluent: toluene/hexane=5/1) to obtain a pale yellow crystal. The crystal was purified by alumina column chromatography (eluent: toluene) and successively recrystallized from ethanol and hexane to obtain 12.4 g of 2-(pyridine-2-yl)-5-methylthiophene (colorless crystal) (Yield: 41.3%).

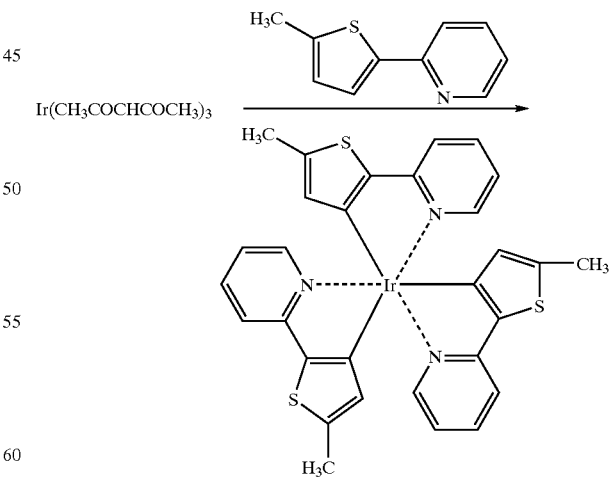

In a 200 ml-four necked flask, 100 ml of glycerol was placed and heat-stirred for 2 hours at 130–140° C. while supplying nitrogen gas therein in the form of bubbles, followed by cooing to 100° C. by standing. To glycerol, 2.10 g (12.0 mM) of 2-(pyridyl-2-yl)-5-methylthiophene and 1.00 g (2.0 mM) of Iridium (III) acetylacetonate were added, followed by heat-refluxing for 8 hours under stirring in nitrogen gas stream.

After the reaction, the reaction mixture was cooled to room temperature and poured into 600 ml of 1N-HCl. The resultant precipitate was recovered by in filtration, washed with water, and dissolved in acetone followed by removal of the insoluble matter by filtration and distilling-off of acetone under reduced pressure to obtain a residue. The residue was purified by silica gel column chromatography (eluent: chloroform) to obtain 0.31 g of Iridium (III) tris[2-(pyridine-2-yl)-5-methylthiophene] (red powder) (Yield: 21.7%).

EXAMPLE 21

Synthesis Compound 15

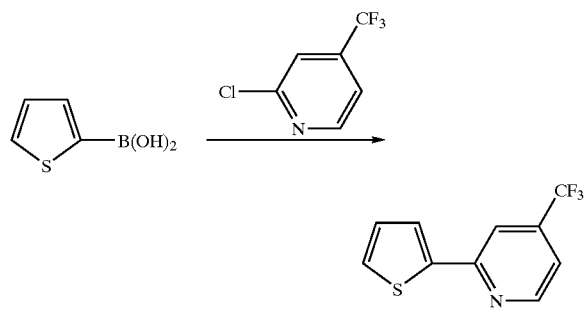

In a 100 ml-three necked flask, 1.73 g (0.95 mM) of 2-chloro-4-trifluoromethylpyridine, 1.23 g (0.96 mM) of thiophene-2-bronic acid, 15 ml of toluene, 7.5 ml of ethanol and 15 ml of 2M-sodium carbonate aqueous solution were placed and stirred in a nitrogen gas stream at room temperature. Under stirring, to the mixture, 0.34 g (0.30 mM) of tetrakis (triphenylphosphine) palladium (0) was added, followed by heat-refluxing for 4 hours and 10 minutes under stirring in nitrogen gas stream.

After the reaction, the reaction mixture was cooled, followed by extraction with cool water and toluene, followed by distilling off of the solvent under reduced pressure to obtain a residue. The residue was purified by silica gel column chromatography (eluent: chloroform) to obtain a pale yellow crystal. The crystal was purified by alumina column chromatography (eluent: toluene) and recrystallized from methanol to obtain 1.98 g of 2-(trifluoromethylpyridine-2-yl)thiophene (Yield: 91.2%).

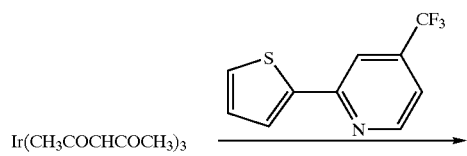

-continued

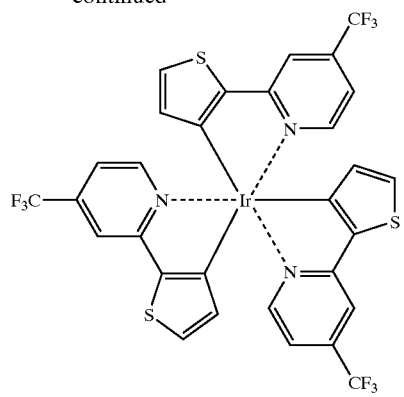

In a 100 ml-four necked flask, 50 ml of glycerol was placed and heat-stirred for 2 hours at 130–140° C. while supplying nitrogen gas therein in the form of bubbles, followed by cooing to 100° C. by standing. To glycerol, 1.20 g (5.2 mM) of 2-(4-trifluoromethylpyridine-2-yl)thiophene and 0.50 g (1.0 mM) of Iridium (III) acetylacetonate were added, followed by heat-refluxing for 8 hours under stirring in nitrogen gas stream.

After the reaction, the reaction mixture was cooled to room temperature and poured into 300 ml of 1N-HCl. The resultant precipitate was recovered by filtration and washed with water, followed by drying for 4 hours at 100° C. under reduced pressure and purification by silica gel column chromatography (eluent: chloroform) to obtain 0.15 g of Iridium (III) tris(2-(4-trifluoromethylpyridine-2-yl)thiophene] (red powder) (Yield: 17.1%).

EXAMPLE 22

Synthesis Compound 16

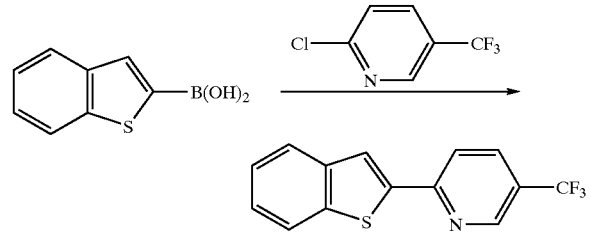

In a 200 ml-four necked flask, 5.16 g (28.4 mM) of 2-chloro-5-trifluoromethylpyridine, 5.06 g (28.4 mM) of benzo[b]thiophene-2-bronic acid, 25 ml of toluene, 12.5 ml of ethanol and 25 ml of 2M-sodium carbonate aqueous solution were placed and stirred in a nitrogen gas stream at room temperature. Under stirring, to the mixture, 1.02 g (0.88 mM) of tetrakis (triphenylphosphine) palladium (0) was added, followed by heat-refluxing for 7.5 hours under stirring in nitrogen gas stream.

After the reaction, the reaction mixture was to cooled on an ice bath to precipitate a crystal. The crystal was recovered by filtration, followed by washing with water and further washing with methanol. The crystal was purified by alumina column chromatography (eluent: chloroform) and recrystallized from chloroform to obtain 2.90 g of 2-(5-trifluoromethylpyridine-2-yl)benzo[b]thiophene (Yield: 36.5%).

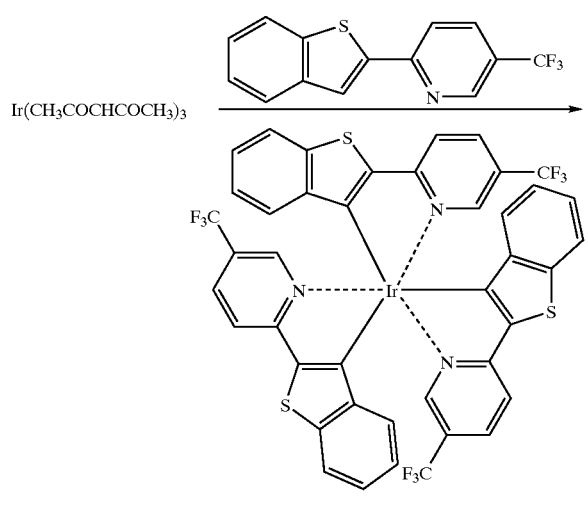

In a 200 ml-four necked flask, 100 ml of glycerol was placed and heat-stirred for 2 hours at 130–140° C. while supplying nitrogen gas therein in the form of bubbles, followed by cooing to 100° C. by standing. To glycerol, 2.82 g (10.1 mM) of 2-(5-trifluoromethylpyridine-2-yl)benzo[b]thiophene and 1.00 g (2.0 mM) of Iridium (III) acetylacetonate were added, followed by heat-refluxing for 8 hours under stirring in nitrogen gas stream.

After the reaction, the reaction mixture was cooled to room temperature and poured into 600 ml of 1N-HCl. The resultant precipitate was recovered by filtration, washed with water, and dissolved in acetone followed by removal of the insoluble matter by filtration and distilling-off of acetone under reduced pressure to obtain a residue. The residue was purified by silica gel column chromatography (eluent: chloroform) to obtain 0.24 g of Iridium (III) tris[2-(5-trifluoromethylpyridine-2-yl)benzo[b]thiophene] (red powder) (Yield: 11.4%).

EXAMPLE 23

With respect to ligands of the metal coordination compounds (Compounds 11, 12, 13 and 16) prepared in Examples 17, 18, 19 and 22, respectively, dipole moments were calculated based on the semi-empirical molecular orbital method (AM1) as to the case where a conformation of respective ligands was such that respective two ring structures connected via a covalent bond were present in an identical plane.

The results are shown in Table 12 together with the corresponding EL device characteristics (peak emission wavelength and luminescence efficiency) shown in Table 11.

TABLE 12

| Compound No. | Dipole-moment (debye) | λPE (nm) | Luminescence efficiency (cd/A) |
|---|---|---|---|
| 11 | 1.8 | 552 | 6.3 |
| 12 | 3.7 | 565 | 4.0 |
| 13 | 1.3 | 600 | 3.1 |
| 16 | 8.6 | 620 | 0.6 |

As shown in Table 12, it has been found that a high-efficiency luminescence was realized in the case where the dipole moment was at most 7 debye, preferably at most 4 debye, and the peak emission wavelength was at least 550 nm.

The described hereinabove according to the present invention, the metal coordination compound of the formula (1) according to the present invention has a higher phosphorescence luminescence efficiency and a shorter phosphorescence life, thus being suitable as a luminescence material for an EL device causing longer-waveform luminescence (orange to red).

The luminescence device (EL device) using the metal coordination compound of formula (1) according to the present invention allows a high-efficiency luminescence at a high luminescence for a long period of time while minimizing luminescence deterioration in energized state.

What is claimed is:

1. A luminescence device, comprising an organic compound layer comprising at least one species of a metal coordination compound according to any one of formulas (1) or (4):

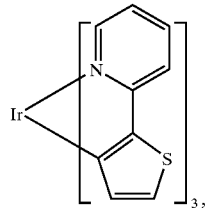

(1)

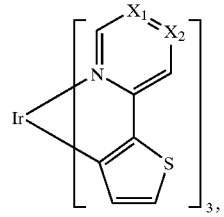

(4)

wherein one of $X_1$ and $X_2$ of the compound of said formula (4) is a nitrogen atom and one of $X_1$ and $X_2$ is a carbon atom, and wherein a hydrogen atom in ligands of said formulas (1) and (4) may optionally be replaced with a substituent selected from the group consisting of a halogen atom; a trialkylsilyl group containing three linear or branched alkyl groups each independently having 1–8 carbon atoms; and a linear or branched alkyl group having 1–20 carbon atoms, which can include at least one methylene group, or at least two non-neighboring methylene groups, which can be replaced with —O—, —S—, —C(O)—, —C(O)—O—, —O—C(O)—, —CH=CH— or —C≡C—, and optionally including a hydrogen atom, which can be replaced with a fluorine atom, with the proviso that a ligand of the compound of said formula (1) has at least one of said linear or branched alkyl groups having 1–20 carbon atoms having at least one hydrogen atom replaced with a fluorine atom.

2. The device according to claim 1, wherein the metal coordination compound is the compound of said formula (1).

3. The device according to claim 1, wherein the metal coordination compound is the compound of said formula (4).

4. The device according to claim 1, wherein the device emits light exhibiting an emission spectrum peak wavelength of at least 550 nm.

5. The device according to claim 1, wherein the metal coordination compound contains a ligand having a dipole moment of at most 7 debye.

6. A flat panel display comprising a luminescence device according to claim 1.

* * * * *